(12) United States Patent
Løype et al.

(10) Patent No.: US 11,737,736 B2
(45) Date of Patent: Aug. 29, 2023

(54) ULTRASOUND IMAGING PROBE WITH IMPROVED HEAT DISSIPATION

(71) Applicant: GE Precision Healthcare LLC, Wauwatosa, WI (US)

(72) Inventors: Birger Løype, Horten (NO); Warren Lee, Niskayuna, NY (US); Stephen D. Edwardsen, Revetal (NO)

(73) Assignee: GE Precision Healthcare LLC, Wauwatosa, WI (US)

( * ) Notice: Subject to any disclaimer, the term of this patent is extended or adjusted under 35 U.S.C. 154(b) by 0 days.

(21) Appl. No.: 17/345,136

(22) Filed: Jun. 11, 2021

(65) Prior Publication Data
US 2022/0395256 A1 Dec. 15, 2022

(51) Int. Cl.
*A61B 8/00* (2006.01)
*A61B 8/14* (2006.01)
*A61B 8/12* (2006.01)
*H05K 7/20* (2006.01)

(52) U.S. Cl.
CPC ............... *A61B 8/546* (2013.01); *A61B 8/12* (2013.01); *A61B 8/14* (2013.01); *H05K 7/2039* (2013.01)

(58) Field of Classification Search
CPC ......... A61B 8/546; A61B 8/12; A61B 8/4455; A61B 8/4444; A61B 8/4494; H05K 7/2039
See application file for complete search history.

(56) References Cited

U.S. PATENT DOCUMENTS

| 10,779,801 B2 | 9/2020 | Pelissier et al. |
| 2002/0055693 A1* | 5/2002 | Thompson .............. A61N 7/00 601/2 |
| 2007/0160858 A1* | 7/2007 | Fukuda ................ H01L 23/053 257/E23.188 |
| 2009/0062656 A1* | 3/2009 | Hyuga .................. A61B 8/445 600/459 |
| 2013/0225995 A1 | 8/2013 | Hashiguchi |
| 2013/0303918 A1 | 11/2013 | Miyajima et al. |
| 2015/0289854 A1* | 10/2015 | Cho ..................... H05K 1/0204 600/463 |
| 2016/0041129 A1 | 2/2016 | Cho et al. |
| 2016/0174939 A1* | 6/2016 | Cho ..................... B06B 1/0629 600/459 |
| 2017/0164926 A1 | 6/2017 | Spicci et al. |
| 2018/0078240 A1* | 3/2018 | Pelissier .............. A61B 8/4444 |
| 2019/0117200 A1* | 4/2019 | Morimoto ............ A61B 8/546 |
| 2019/0231309 A1* | 8/2019 | Gu ......................... F28D 21/00 |

FOREIGN PATENT DOCUMENTS

| JP | 2019-097722 A | 6/2019 |
| WO | 2018120770 A1 | 7/2018 |

\* cited by examiner

*Primary Examiner* — Joel Lamprecht
(74) *Attorney, Agent, or Firm* — Boyle Fredrickson, S.C.

(57) ABSTRACT

An ultrasound imaging device or probe includes a tip having a heat conducting exterior housing within which an imaging element is positioned. The imaging element is engaged with a heat sink formed of an electrically insulating material that also has high thermal conductivity. The heat sink contacts and extends through and electrically insulating enclosure within which the imaging element is disposed. As a result, the heat generated by the imaging element can be readily conducted to the ambient environment via the heat sink and heat conductive exterior housing while also enabling the imaging element and other electrical components to be electrically insulated from the housing.

18 Claims, 7 Drawing Sheets

ULTRASOUND IMAGING PROBE WITH IMPROVED HEAT DISSIPATION

BACKGROUND OF THE INVENTION

Embodiments of the present disclosure relate generally to ultrasound imaging probes and, more particularly, to heat dissipating structures of ultrasound imaging probes.

Various medical conditions affect internal organs and bodily structures. Efficient diagnosis and treatment of these conditions typically require a physician to directly observe a patients internal organs and structures. On many occasions, imaging using an ultrasound imaging system is utilized to obtain images of a patient's internal organs and structures in a minimally invasive manner. The ultrasound images can be obtained utilizing a probe that is located either externally or internally relative to the patient.

By way of example, ultrasound images for non-interventional procedures, such as those obtained for transthoracic echocardiography (TTE), can be obtained by placing the probe against the exterior of the chest of the patient when operating the ultrasound imaging system. Alternatively, ultrasound images for interventional procedures, such as for transesophageal echocardiography (TEE) and/or intracardiac echocardiography (ICE), are obtained by inserting the probe within the body of the patient, e.g., into the esophagus, while the ultrasound imaging system is in operation.

Ultrasound procedures are typically performed in examination, intervention and operating room (open heart surgery) situations where imaging of internal structures of the patient is required. The device utilized in performing the ultrasound procedure typically includes the probe, a processing unit, and a monitor. The probe is connected to the processing unit which in turn is connected to the monitor. In operation, the processing unit sends a triggering signal to the probe. The probe then emits ultrasonic signals via an imaging element within the probe into the patient. The probe then detects echoes of the previously emitted ultrasonic signals. Then, the probe sends the detected signals to the processing unit which converts the signals into images. The images are then displayed on the monitor.

Typically, during the operation of the ultrasound imaging system, the emission of the ultrasonic signals via an imaging element disposed at or near the tip of the probe generates an amount of heat from the imaging element within the probe. In addition, some advanced probes contain application specific integrated circuits (ASICs) with electronics for transmitting and receiving signals from the imaging element. These ASICs also dissipate power and generate heat. Further, the more power utilized by the imaging element and associated ASIC to emit the ultrasonic signals, which enhances the quality of the obtained images, the more heat is generated by the imaging element and ASIC. In order to dissipate the heat and comply with regulatory requirements limiting the maximum temperature of the probe, as shown in FIG. 1, prior art probes 10 include a plastic housing 12 around the tip 11 of the probe 10 that enables the heat to be passively conveyed through the housing 12 and into the ambient environment around the probe, e.g., the air and/or patient skin for an externally positioned probe, or the esophagus tissue for an internally disposed probe. During operation, the heat generated by the imaging element 13, such as a matrix array transducer 14 and associated application-specific integrated circuit (ASIC), 16, can be conducted directly to and through the housing 12, such as directly through a plastic acoustic lens 18 forming a part of the plastic housing 12, or through an acoustic backing layer 19 to a heat sink 20 disposed within the probe housing 12 and thermally coupled between the imaging element 13 and the housing 12, e.g., by a heat spreader 22 which also functions as an electromagnetic interference (EMI) shield, to direct or conduct heat away from the imaging element 13.

Plastic is primarily utilized for the probe housing construction for its ability to electrically insulate the interior components of the probe from the patient tear safety purposes. However, while heat can be conveyed through the plastic housing, the low thermal conductivity of the plastic material forming the housing places significant restrictions on the amount of heat generated by the imaging element 13 that can be dispersed by the plastic housing. In addition, to enhance the robustness of the probe 10 and to accommodate the required creepage distance for electrical insulation purposes, in many probes 10 the plastic housing 12 is Harmed to be relatively thick, increasing the durability of the probe but consequently reducing the thermal conductivity of the housing 12 and therefore inhibiting heat transfer out of the probe 10.

Also, the heat sink 20 is thermally coupled to the imaging element 13 and to the heat spreader 25. The heat spreader 25 must be bonded to the outer plastic housing 12 with an adhesive 24, adding more thermal resistance to the conduction of heat away from the imaging element 13 through the housing 12. As such, the power output of prior art probes 10, and corresponding image quality, is necessarily limited by the thermal conductivity of prior art probe structures.

In addition, while various active cooling systems have been developed for placement within the probe 10 to increase the amount of heat dissipation capable for the probe beyond the capabilities of the passive dissipation achieved through the housing 12, these cooling systems greatly increase the complexity and associated cost of the probe construction. Further, for interventional or intend probes, the size of the probe 10 required for insertion within the body of the patient, i.e., into the esophagus, does not have space available for a cooling system to be positioned within the probe housing.

Therefore, it is desirable to develop a structure for an ultrasound probe that increases the thermal conductivity of the probe when in operation. The improved thermal conductivity of the probe structure enables probes with smaller sizes to be formed that have emission areas similar to prior art probes, as well as allowing increased power to be utilized by the probe for ultrasound signal emission to significantly improve the quality of the resulting images obtained by the probe.

BRIEF DESCRIPTION OF THE DISCLOSURE

In one exemplary embodiment of the invention, an ultrasound imaging probe includes an imaging element, an electrically insulating enclosure disposed around the imaging element, the insulating enclosure including a heat sink operably engaged with the imaging element, the heat sink formed of an electric insulating and heat conductive material, and a heat conductive housing disposed around the insulating enclosure and in contact with the heat sink.

In another exemplary embodiment of the invention, an ultrasound imaging probe includes an imaging element having a transducer element and a heat sink operably engaged with the transducer element, the heat sink formed of an electrically insulating and heat conductive material, an electrically insulating enclosure disposed around the imaging element and a housing disposed around the insulating enclosure, wherein a portion of the heat sink extends through the insulating enclosure into contact with the housing.

In a further exemplary embodiment of the invention, an ultrasound imaging system includes a processing unit configured to receive and process acquired ultrasound image data to create ultrasound images derived from the ultrasound image data, a display operably connected to the processing unit to present the created ultrasound images to a user, and an ultrasound imaging probe operably connected to the processing unit to obtain the ultrasound image data, the ultrasound imaging probe having an imaging element with a transducer element and a heat sink operably engaged with the transducer element, the heat sink formed of an electrically insulating and heat conductive material, an electrically insulating enclosure disposed around the imaging element, and a heat conductive housing disposed around the insulating enclosure, wherein a portion of the heat sink extends through the insulating enclosure into contact with the housing.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

FIG, 3 illustrates an exemplary ultrasound imaging system 100 for optimal visualization of a target structure 102 for use during ultrasound imaging procedures. For discussion purposes, the system 100 is described with reference to a TEE probe utilized with the system 100. However, in certain embodiments, other types if imaging probes may be employed with the imaging system 100, such as a TIE probe, or an ICE probe, among others.

In one embodiment, the ultrasound imaging system 100 employs ultrasound signals to acquire image data corresponding to the target structure 102 in a subject. Moreover, the ultrasound imaging system 100 may combine the acquired image data corresponding to the target structure 102, for example the cardiac region, with supplementary image data. The supplementary image data, for example, may include previously acquired images and/or real-time intra-operative image data generated by a supplementary imaging system 104 such as a CT, MRI, PET, ultrasound, fluoroscopy, electrophysiology, and/or X-ray system. Specifically, a combination of the acquired image data, and/or supplementary image data may allow for generation of a composite image that provides a greater volume of medical information for use in accurate guidance for an interventional procedure and/or for providing more accurate anatomical measurements.

Figure 1:
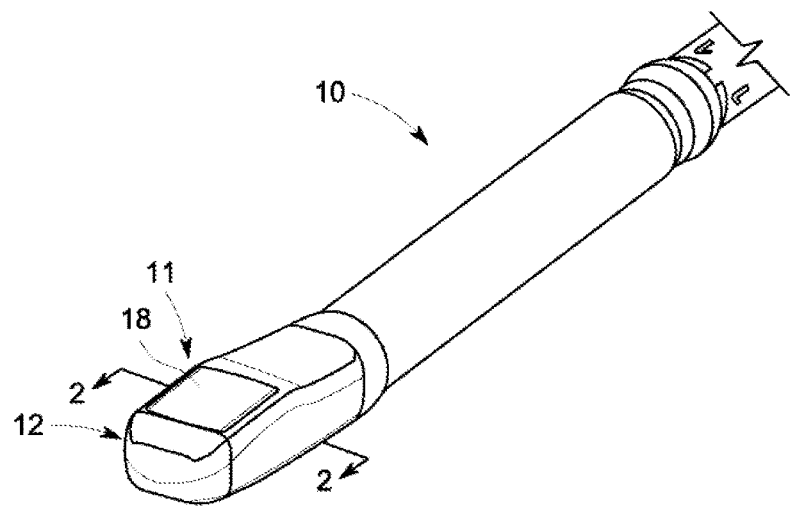
FIG. 1 is an isometric view of a prior art ultrasound probe.
Figure 2:
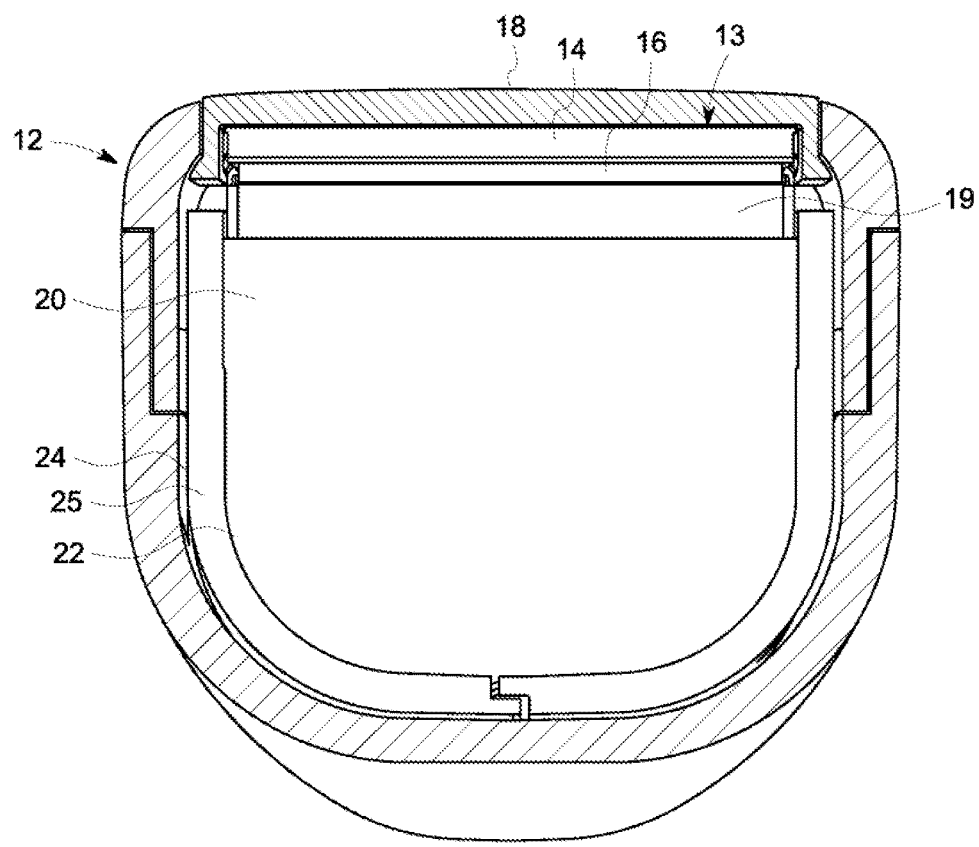
FIG. 2 is a cross-sectional view along line-2-2 of the prior art ultrasound probe of FIG. 1.
Figure 3:
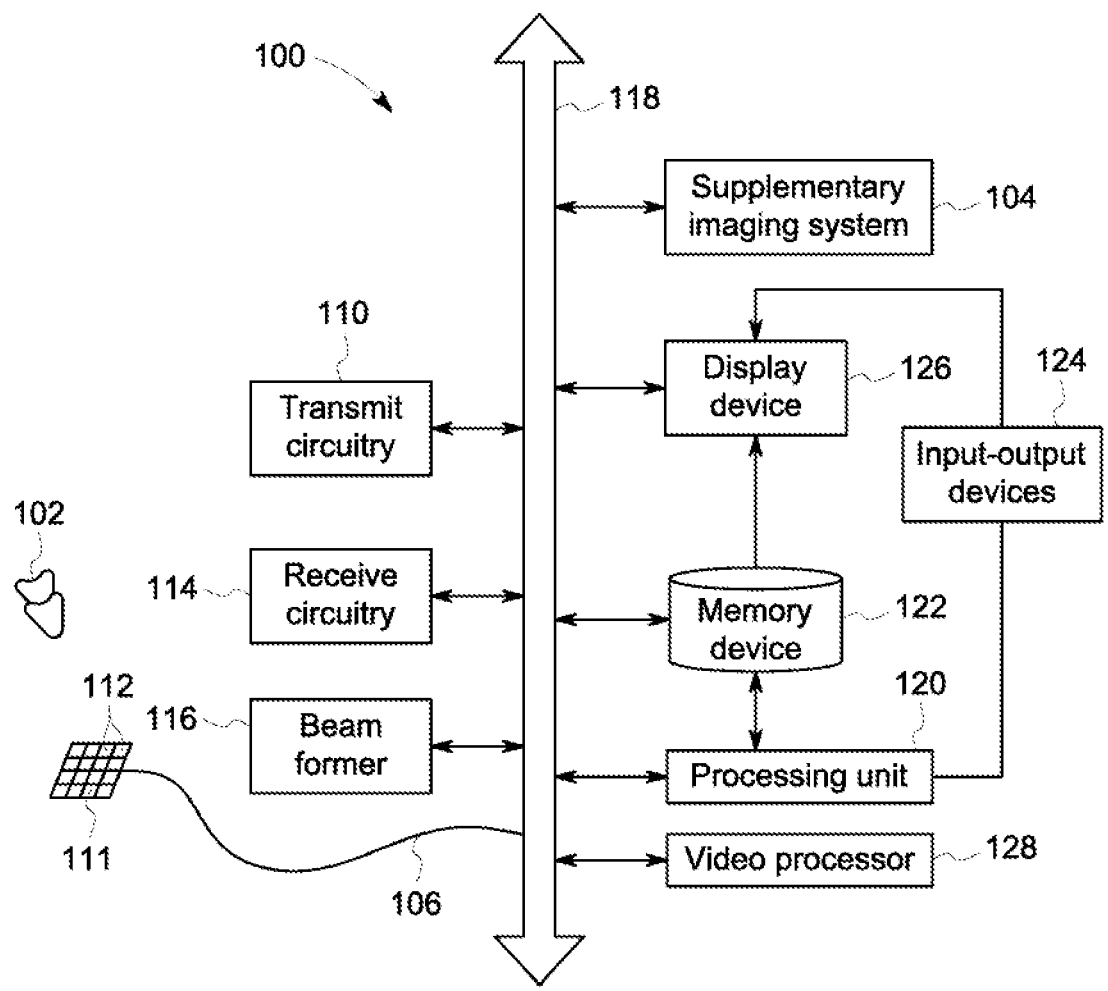
FIG. 3 is a schematic view of an ultrasound imaging system according to an embodiment of the disclosure.
Figure 4:
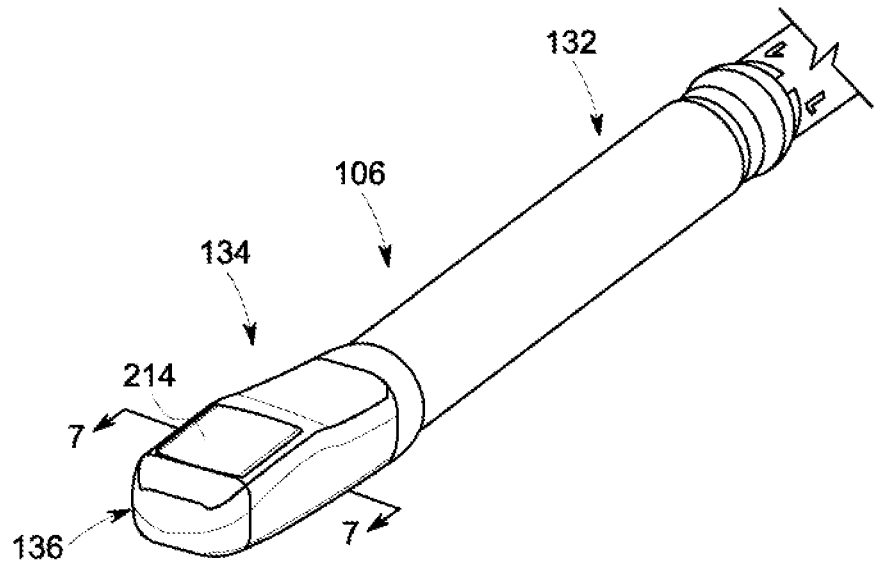
FIG. 4 is an isometric view of an ultrasound probe according to an exemplary embodiment of the disclosure.
Figure 5:
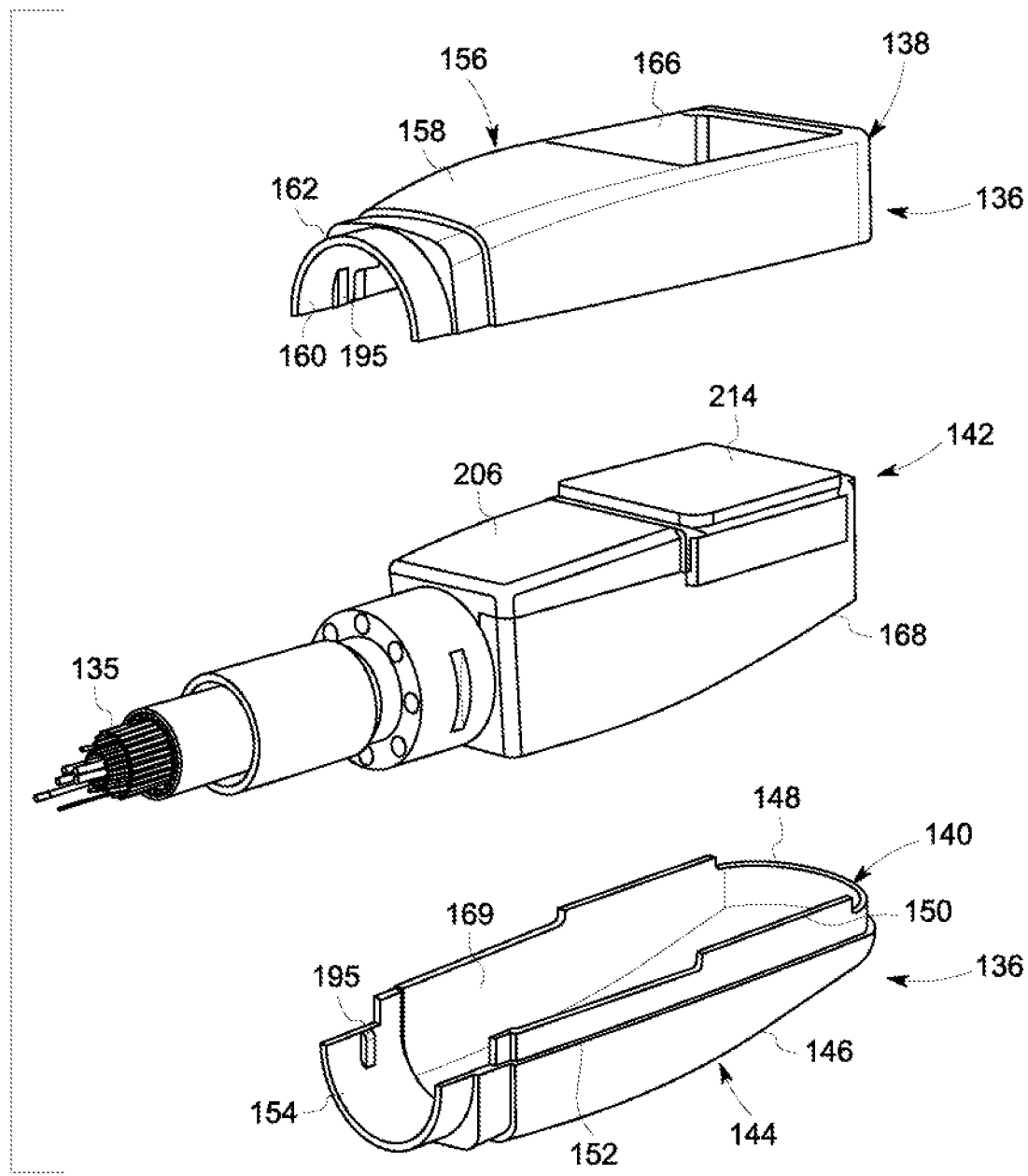
FIG. 5 is a partially broken away, exploded view of a tip of the probe of FIG. 4.

Accordingly, in one embodiment shown in FIG. 4, the ultrasound imaging system 100 includes an interventional device or probe 106 such as an ultrasound probe, a laparoscope, a bronchoscope, a colonoscope, a needle, a catheter and/or an endoscope. The probe 106 is adapted for external use, i.e., the probe 106 is placed on the skin of the patient to image internal structures of the patient, or the probe 106 can be configured to be operated in a confined medical or surgical environment such as a body cavity, orifice, or chamber corresponding to a subject, e.g., the patient.

Figure 6:
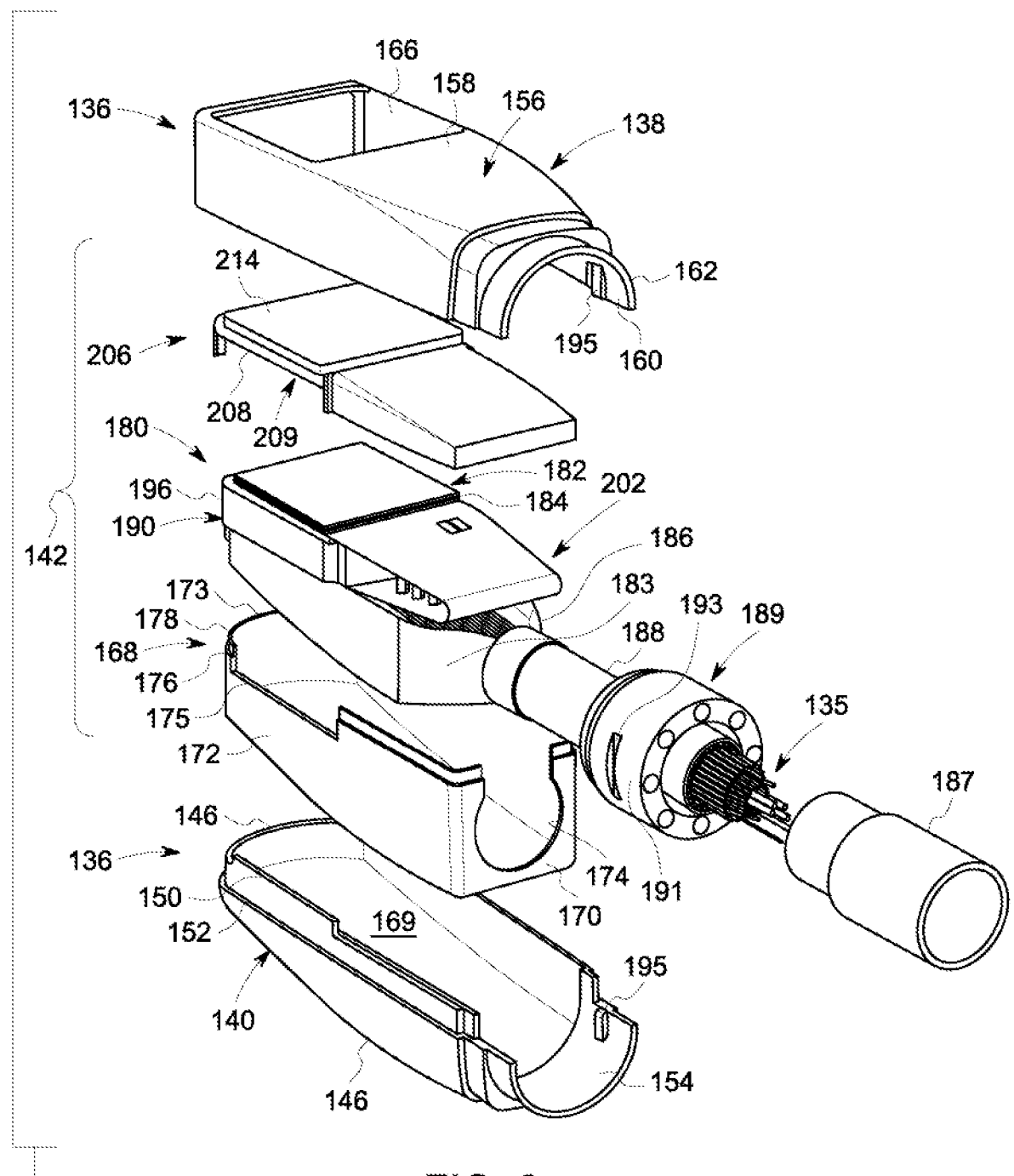
FIG. 6 is an exploded view of the tip of FIG. 5.

To that end, in certain embodiments shown in FIG. 6, the ultrasound imaging system 100 includes transmit circuitry 110 that may be configured to generate a pulsed waveform to operate or drive an imaging element 180, such as one or more transducer elements 182 or a transducer array 184, as controlled by the user via the system 100, or a control device or handle (not shown) operatively connected to the imaging element 180 as part of the system 100. The transducer elements 182 are configured to transmit and/or receive ultrasound energy and may comprise any material that is adapted to convert a signal into acoustic energy and/or convert acoustic energy into a signal. For example, the transducer elements 182 may be a piezoelectric material, such as lead zirconate titanate (PZT), or a capacitive micromachined ultrasound transducer (CMUT) according to exemplary embodiments. The interventional device 106 may include more than one transducer element 182, such as two or more transducer elements 182 optionally arranged in a matrix transducer array 184, or separated from each other on the interventional device 106. The transducer elements 182 produce echoes that return to the transducer elements 182/array 184 and are received by receive circuitry 114 for further processing. The receive circuitry 114 may be operatively coupled to a beamformer 116 that may be configured to process the received echoes and output corresponding radio frequency (RF) signals.

Further, the system 100 includes a processing unit 120 communicatively coupled to the beamformer 116, the interventional device/probe 106, and/or the receive circuitry 114, over a wired or wireless communications network 118. The processing unit 120 may be configured to receive and process the acquired image data, for example, the RF signals according to a plurality of selectable ultrasound imaging modes in near real-time and/or offline mode.

Moreover, in one embodiment, the processing unit 120 may be configured to store the acquired volumetric images, the imaging parameters, and/or viewing parameters in a memory device 122. The memory device 122, for example, may include storage devices such as a random access memory, a read only memory, a disc drive, solid-state memory device, and/or a flash memory. Additionally, the processing unit 120 may display the volumetric images and or information derived from the image to a user, such as a cardiologist, for further assessment on a operably connected display 126 for manipulation using one or more connected input-output devices 124 ton communicating information and/or receiving commands and inputs from the user, or for processing by a video processor 128 that may be connected and configured to perform one or more functions of the processing unit 120. For example, the video processor 128 may be configured to digitize the received echoes and output a resulting digital video stream on the display device 126.

Looking now at the exemplary illustrated embodiment of FIGS. 4-7, the probe 106, such as a transesophageal echocardiography (TEE) probe, is connected to the imaging system 100 and is operable via the system 100 or a control handle (not shown) to control the function and/or movement of the probe 106. The probe 106 includes an insertion tube 132 that encloses the signal transmission and control/power wiring 135 extending between the system 100 and the probe tip 134, as well as the movement mechanism(s) for articulating the tube 132 within the patient.

Looking now at FIGS. 4-7, the tip 134 includes a housing 136 having a top portion 138 and a bottom portion 140 joined to one another about an electrically insulating inner enclosure 142. The top portion 138 and the bottom portion 140 of the housing 136 are each formed of a material having a high thermal conductivity, such as a metal material including but not limited to gold, silver, aluminum, magnesium, stainless steel, titanium, nickel, copper and/or brass with biocompatible plating, and their alloys. The bottom portion 140 includes a body 144 that conforms to the shape of the insulating enclosure 142 and is formed with a closed lower end 146 and an open upper end 148. The body 144 also includes a lip 150 on the upper end 148 of the body 144 and spaced inwardly from a peripheral edge 152 of the upper end 148. The lip 150 extends around the perimeter of the body 144 between opposite sides of a cable collar 154 formed at one end of the body 144.

The top portion 138 is formed similarly to the bottom portion 140 with a body 156 that conforms to the shape of the insulating enclosure 142, the body 156 having a closed upper end 158, an open lower end 160 and a cable collar 162 disposed at one end of the body 156. The lower end 160 of the body 156 of the top portion 138 is dimensioned to closely conform to the lip 150 of the bottom portion 140 when the top portion 138 and bottom portion 140 are assembled to form the housing 136, such that the lower end 160 of the top portion 138 contacts the peripheral edge 152 of the bottom portion 140 and overlaps the lip 150 with a minimal gap 164 formed therebetween.

The top portion 138 also includes an aperture 166 formed in the closed upper end 158 generally opposite the cable collar 162. The aperture 166 receives a portion of the insulating enclosure 142 therein in order to enable ultrasound signals to be emitted from and received by the insulating enclosure 142 through the housing 136.

Figure 7:
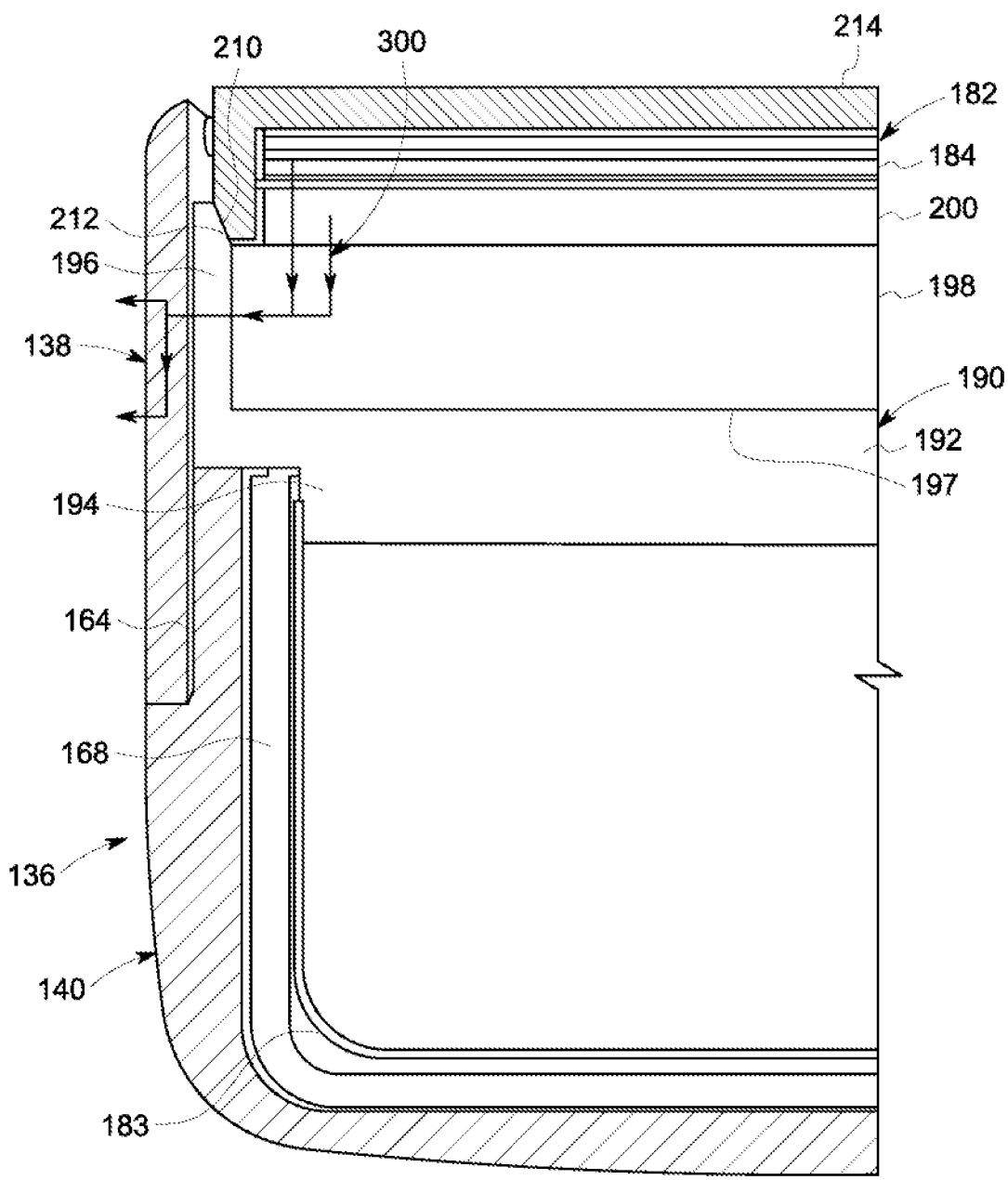
FIG. 7 is a cross-sectional view along line 7-7 of FIG. 4.

Referring now to FIGS. 6 and 7, the insulating enclosure 142 includes an insulating body 168 corresponding in shape to the interior 169 of the bottom portion 140 and formed with a closed bottom surface 170 and a peripheral side wall 172 extending around the bottom surface 170 to define an open upper end 173. The insulating body 168 in the exemplary illustrated embodiment is formed of an electrically insulating material, such as a plastic material, and includes a notch 174 formed in the side wall 172 in alignment with the cable collar 154 disposed on the bottom portion 140.

The side wall 172 additionally includes a pair of recesses 175 formed therein. While one or more recesses 175 can be present, in the illustrated exemplary embodiment the pair of recesses 175 are disposed in alignment with one another on opposed sides of the insulating body 168 and extend downwardly into the side wall 172 from a peripheral edge 176 of the side wall 172. The remainder of the side wall 172 includes a peripheral lip 178 spaced inwardly from the peripheral edge 176 and extending upwardly from the side wall 172.

Within the insulating body 168 is disposed the ultrasound imaging element 180. The imaging element 180 may be configured to generate cross-sectional images of the target structure 102 for evaluating one or more corresponding characteristics. Particularly, in one embodiment, imaging element 180 is configured to acquire a series of three-dimensional (3D) and/or four-dimensional (4D) ultrasound images corresponding to the subject, though the imaging element 180 can also obtain one-dimensional (1D) and two-dimensional (2D) ultrasound images. In certain embodiments, the imaging system 100 may be configured to generate the 3D model relative to time, thereby generating a 4D model or image corresponding to the target structure, such as the heart of the patient. The imaging system 100 may use the 3D and/or 4D image data, for example, to visualize a 4D model of the target structure 102 for providing a medical practitioner with real-time guidance for navigating the probe/interventional device 106 on or within the patient.

As best shown in FIGS. 6 and 7, the imaging element 180 includes an electromagnetic interference (EMI) shield 183 as a component of the imaging element 180. The EMI shield 183 in the illustrated exemplary embodiment is thrilled of a metal material which operates to prevent interference with the signals being received by the imaging element 180 for the ultrasound images. The EMI shield 183 conforms closely in shape to the interior 184 of the insulating body 168 and defines an open upper end 186. The EMI shield 183 also includes an EMI cable shield 188, optionally formed integrally therewith, that extends outwardly from EMI shield 183 to be positioned through the notch 174 in the insulating body 168 and enclose the signal and power wiring 135 extending from the imaging element 180 and into the insertion tube 132. A flange 189, formed as a part of the insulating enclosure 142, can be positioned around the EMI cable shield 188 and around the notch 174 to facilitate electrical insulated attachment of the insertion tube 132. The insertion tube is made of metal and for risk mitigation we need the insertion tube to be electrically insulated from the metal housing. The flange 189 can be formed of a different material, such as an electric insulating material, e.g., plastic or ceramic, and can be formed with engagement structures 191 thereon, such as slots 193, that receive complementary tabs 195 formed on the cable collars 154, 162 to assist in aligning and securing the top portion 138 and bottom portion 140 of the housing 136 around the insulating enclosure 142, thereby completely insulating the housing 136 from the imaging element 180 within the insulating enclosure 142, i.e., rendering the housing 136 electrically floating relative to the imaging element 180. The flange 189 may also be an integrated part of the metal housing 136 if it is, for example, an insulated material that is glued or overmolded to the metal housing 136.

The imaging element 180 further includes a heat sink 190 extending across the insulating body 168 and contacting the open upper end 186 of the EMI shield 183. The heat sink 190 is thrilled of a material that has a high thermal or heat conductivity, e.g., at least 2.0 W/(mK), or in other embodiments at least 20.0 W/(mK), but that is also electrically insulating, such as certain ceramic materials. In one exemplary embodiment, the ceramic material is selected from di-electric ceramics with high thermal conductivity including but not limited to, aluminum nitride, silicon nitride or silicon carbide.

As best shown in FIG. 7, the heat sink 190 includes a central portion 192 extending between and contacting the recesses 175 in the insulating body 168, a lower portion 194 extending downwardly from the central portion 192 between the side walls 172 of the insulating body 168 into contact with the EMI shield 183, and number of side panels 196 extending upwardly from the sides of the central portion 192 and defining a cavity or channel 197 therebetween. The panels 196 adjacent each recess 175 are each positioned in direct thermal contact with the lip 150 of the bottom portion 140 and with the interior surface of the body 156 of the top portion 138.

Between the panels 196 and above the central portion 192 in the cavity 197, the heat sink 190 supports a layer of acoustic backing material 198. The material forming the acoustic backing layer 198 has a high thermal conductivity of at least 2 W/(mK) and supports an application-specific integrated circuit (ASIC) 200 thereon opposite the central portion 192 of the heat sink 190. The ASIC 200 supports the one or more transducer elements 182 array 184 opposite the backing layer 198 and is operably connected to a flexible electronic circuit 202 disposed between the ASIC 200 and the acoustic stack/elements 182/array 184. The flexible circuit 202 extends away from and around the heat sink 190 for connection to the signal and power wiring 135 to supply control signals and power from the wiring 135 to the ASIC 200 and the transducer elements 182/array 184 in order to operate the transducer elements 182/army 184 as desired to obtain the ultrasound images of the target structure 102.

To insulate the transducer elements 182/array 184, ASIC 200 and flexible circuit 202 forming parts of the imaging element 180 within the insulating enclosure 142, a cover 206 formed of an electrically insulating material, such as a plastic material, is disposed in engagement with the open upper end 173 of the insulating body. The cover 206 is shaped to be complementary to the configuration of the insulating body 168 to form the insulating enclosure 142 to electrically insulate the imaging element 180 disposed therein, along with sufficient thickness in the body 168 and cover 206 and/or their overlapping components to accommodate for the required creepage distance in the insulating enclosure 142. In the exemplary illustrated embodiment best shown in FIGS. 5-7, the cover 206 includes a pair of side or second recesses 208 aligned with the first recesses 175 in the insulating body 168 to define an opening 209 in the insulating enclosure 142. The recesses 208 are dimensioned to engage and position the panels 196 of the heat sink 190 on the exterior of the insulating enclosure 142, where the panels 196 essentially form a part of the exterior of the insulating enclosure 142 while electrically insulating the remainder of the imaging element 180 within the insulating enclosure 142. The recesses 175 include tapered lower edges 210 that are positioned against complementary shaped surfaces 212 on the interior of the panels 196 that allow the recesses 175 to be placed in close proximity to the backing layer 198, maximizing the insulating properties of the cover 206.

Further, to assist in the focusing of the ultrasound signals generated and received by the transducer elements 182/array 184, a portion of the cover 206 disposed over the transducer elements 182/array 184 is formed as an acoustic lens 214. The shape of the lens 214 corresponds to the shape of the aperture 166 in the top portion 138 of the housing 136, such that the ultrasound signals can pass unobstructed through the housing 136.

In operation, when the probe 106 is positioned on the patient to obtain ultrasound images of internal structure(s) 102, e.g., against the skin or into the esophagus of the patient, power is supplied to the imaging element 180 to generate ultrasound signals from the transducer elements 182/array 184. Concurrently, the electric insulating properties of the materials forming the various components of the insulating enclosure 142, i.e., insulating body 168, flange 189, the cover 206, and panels 196 of the heat sink 190, negate any path for electricity to be conducted outside of the insulating enclosure 142 to the patient. As such, the metal housing 136 is electrically isolated, or body floating, from the EMI shields 183,188 and the electric circuit 202 disposed within the insulating enclosure 142 of the probe 106.

Further, while in operation the heat generated by the transducer elements 182/array 184 and/or the ASIC 200 is conducted through the insulating enclosure 142 along a heat path 300 to the ambient for dissipation. As shown in FIG. 7, the heat path 300 is defined from the ASIC 200 though the backing layer 198, the heat sink 190/panels 196 and ultimately the metal housing 136 onto the tissue of the patient surrounding the probe 106. Additional heat dissipation occurs through the bottom portion 140 of the housing 138 since it is in thermal contact with the top portion of the housing 136. As a result of the high thermal conductivity/ low thermal resistance of each of the components of the probe 106 forming the heat path 300, the increased rate of heat dissipation along the heat path 300 enables increased power to be supplied to the transducer elements 182/array 184 of the probe 106 to obtain higher quality images.

In addition to the improved heat dissipation properties provided by the material forming the housing 136, e.g., the metal, the durability of the metal enables the thickness of the housing 136 to be significantly reduced in comparison with prior art plastic probe housings. This, in turn, results in a smaller cross-sectional area for the probe 106, so that smaller probes 106 can be operated at greater power to obtain higher quality images within a highly durable housing 136.

Figure 8:
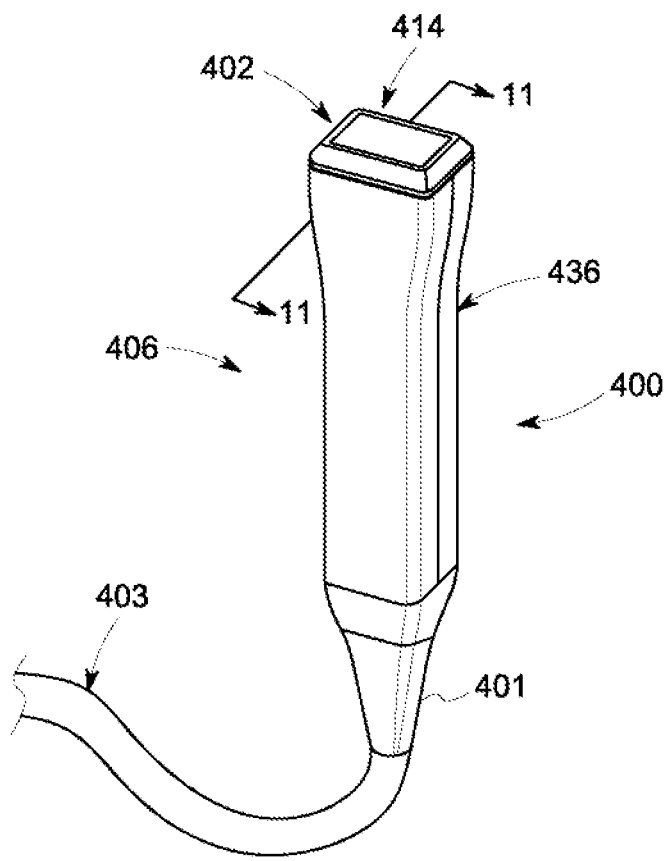
FIG. 8 is an isometric view of an ultrasound probe according to another exemplary embodiment of the disclosure.
Figure 9:
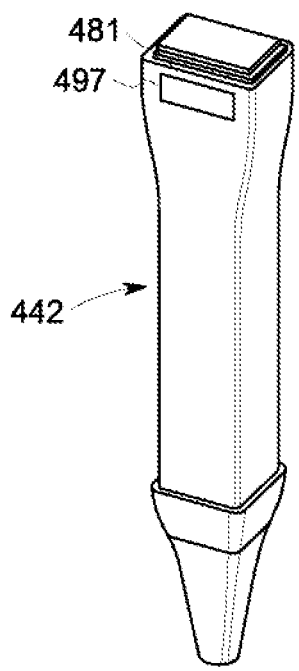
FIG. 9 is an isometric view of the probe of FIG. 8 with the outer housing removed.
Figure 10:
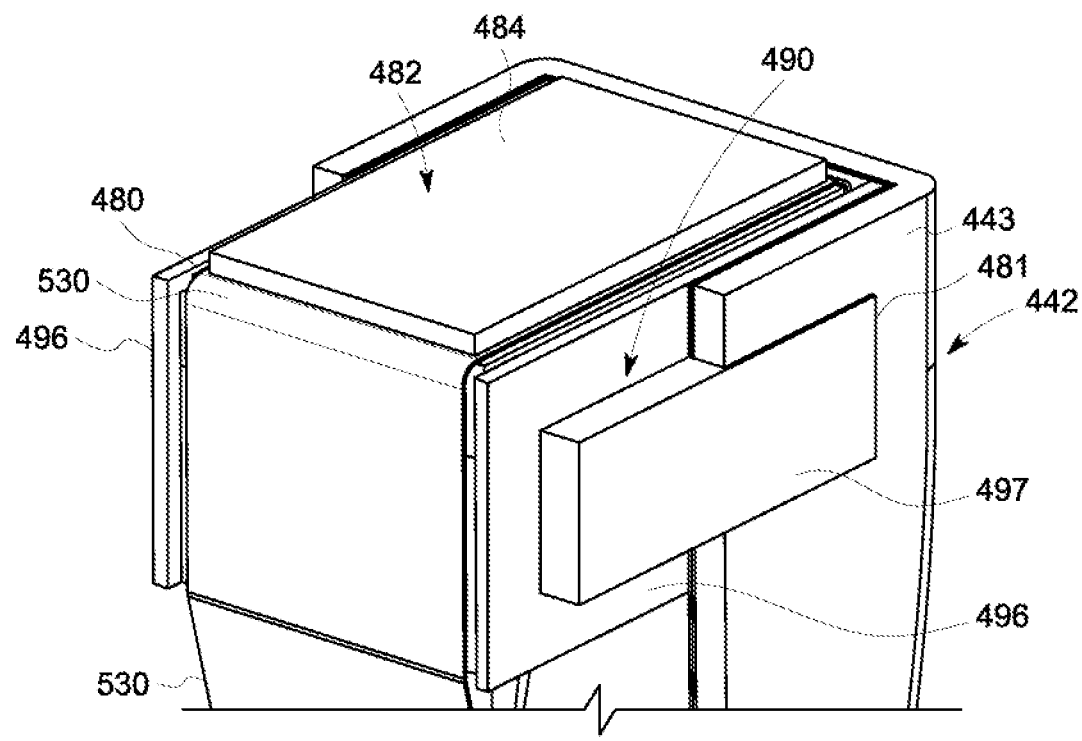
FIG. 10 is a partially broken away, isometric view of an imaging end of the probe of FIG. 9.

In an alternative exemplary embodiment as shown in FIGS. 8-10, the probe 406 can be constructed for external use, such as a transthoracic echocardiography (TTE) probe with a convex, linear or other configuration, that is constructed similarly to TEE probe 106, but where tip 414 functions as a handle or wand 400 that is grasped directly by a user to position the probe 406 against the exterior/skin of the patient for imaging internal target structures 102 of the patient. The handle 400 includes a connector 401 at one end that is connected to the imaging system 100 via a wiring sheath 403 that encloses signal and power wiring (not shown) for operation of the probe 406, and an imaging end 402 disposed opposite the connector 401. As shown in FIGS. 8 and 9, the probe 406 includes an electrically insulating inner enclosure 442 and a thermally conductive housing 436 forming the exterior of the handle 400 that conforms to the shape of the enclosure 442. The housing 436, which is formed similarly to housing 136, e.g., formed of a metal material, defines an aperture 466 at the imaging end 402 through which ultrasound signals are transmitted and received during operation of the probe 406 to obtain ultrasound images.

Figure 11:
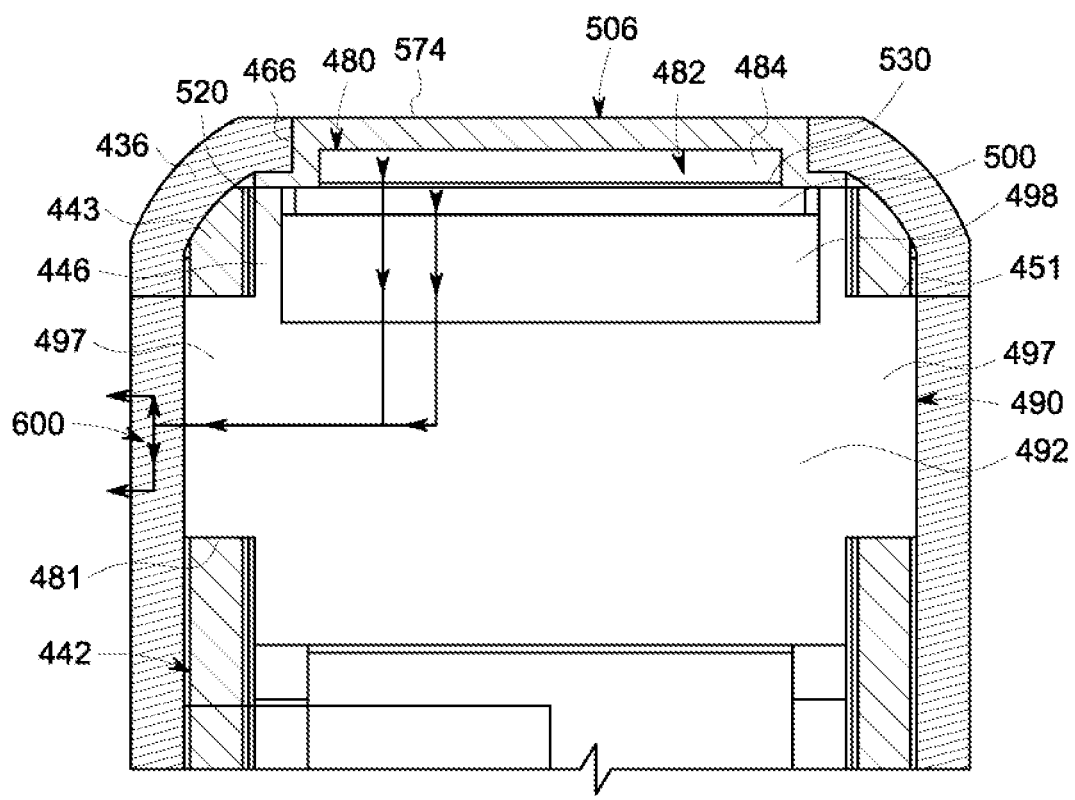
FIG. 11 is a partially broken away, cross-sectional view along line 10-10 of FIG. 8.

Referring specifically to the exemplary embodiment illustrated in FIGS. 9-11. The enclosure 442 is formed of one or more components 443 of an electrically insulating material, such as a plastic, that are engaged or formed with the connector 401 with sufficient thickness in the components 403 or their overlapping portions to accommodate for the required creepage distance in the insulating enclosure 442. The enclosure 442 extends away from the connector 401 towards the imaging end 402 and defines a one or more openings 481 adjacent the imaging end 402 on one or more sides of the enclosure 442, e.g., on opposed sides of the enclosure 442. At the imaging end 402, the enclosure 442 includes an electrically insulating cover 506 joined to the components 443 and formed in part by an acoustic lens 574 that projects into the aperture 466 defined by the housing 436.

Within the enclosure 442, an imaging element 480 includes a heat sink 490 is positioned across the enclosure 442 adjacent the cover 506. The heat sink 490 is formed similarly to the heat sink 190, i.e., of at high thermally conductive and electrically insulative material, such as a ceramic material, with a central portion 492 disposed within the enclosure 442 and one or more side panels 496 disposed on the sides of the central portion 492. Each panel 496 includes a projection 497 extending outwardly from the panel 496 into engagement with and through an adjacent opening 481 defined in the enclosure 442. The central portion 492 and side panels 496 additionally define a cavity or channel 520 below the acoustic lens 514 within which an acoustic backing material layer 498 formed form a high thermally conductive material is positioned. On the backing material layer 498 opposite the central portion 492 is disposed an ASIC 500 and one or more transducer elements 482/array 484 forming additional components of the imaging element 480 that are connected with one another, aligned with the lens 514, and operable to emit and receive ultrasound signals through the lens 514. The ASIC 500 and transducer elements 482/array 484 are also connected to a flexible electronic circuit 530. The flexible circuit 530 is secured between and extends from the ASIC 500/transducer elements 482/array 484 around the central portion 492 of the heat sink 490 and along the interior of the enclosure 442 to the connector 401 for connection to the signal and power wiring contained within the sheath 403.

In this construction, the electric circuits formed by the ASIC 500, transducer elements 482/array 484 and the flexible circuit 530 are electrically insulated from the exterior of the probe 406 by the combination of the enclosure 442 and the projections 497 of the heat sink 490 engaged within and extending through the openings 482 in the enclosure 442. Further, the probe 406 defines a heat path 600 that effectively dissipates heat created as a result of the operation of the heat-generating components of the probe 406, i.e., the ASIC 500, and the transducer elements 482/array 484. The heat path 600 is defined from the heat-generating components through the backing material layer 498, into the heat sink 480, and through the projections 497 on the heat sink 480 into the metal housing 436. As the metal housing 436 is in direct contact with the ambient environment, i.e., the air surrounding the probe 406 and/or the skin against which the probe 406 can be placed either on the patient or the user, the high thermal conductivity of the metal housing 436 enables a greater dissipation of heat from the probe 406 with a thinner housing 436 than achievable in prior art probe configurations, While maintaining full electric insulation for the electric circuits disposed within the housing 436 of the probe 406.

In alternative embodiments of the present disclosure, the various components of the probe 106,406 can be secured to one another in any suitable manner that maintains the electric insulation and thermal conductivity attributes of the probe 106,406. In one particular exemplary embodiment, the components can be affixed to one another utilizing any suitable adhesive, such as a high thermal conductivity epoxy (not shown) having a suitable bond line thickness that secures the components to one another without interfering with the electric insulation and thermal conductivity of the components along the heat path 300,600.

In other alternative exemplary embodiments for the probe 106,406, the housing 136 can be formed at least partially of metal and/or to include metal coatings on portions of the housing 136,436 contacting the heat sink 190,490 for improved heat dissipation purposes. Further, the housing 136,436 can be formed from materials other than metals that provide high thermal conductivity to dissipate heat from the probe 106,406. For example, the housing 136 can be formed of a ceramic material similar to that utilized for the heat sink 190,490, thereby maintaining the thermal conductivity of a metal and adding the electric insulation capacity to the housing 136,436. Further, in certain exemplary alternative embodiments the heat sink 190,490 and the housing 136,436 can be formed as a unitary component.

In addition, other alternative exemplary embodiments for the probe 106,406 can include an acoustic hacking layer 198,498 formed integrally with the heat sink 190,490, thereby enhancing the thermal conductivity between the heat generating components, i.e., the ASIC 200/transducer elements 182/array 184, and the heat sink 190,490.

In still other alternative exemplary embodiment, the insulating enclosure 142,442 can be constructed with a portion of the enclosure 142,442 thrilled of an electrically insulating and thermally conductive material, such as a ceramic material. The portion of the insulating enclosure 142,442 can be positioned in contact with the exterior housing 136,436 and in contact with a heat sink 190,490 or other heat conductive component of the imaging element 180/480 to facilitate heat dissipation through the insulating enclosure 142,442.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasound imaging probe comprising:
    an imaging element comprising:
        a transducer element; and
        a heat sink operably engaged with the transducer element, the heat sink formed of an electrically insulating and heat conductive material;
    an electrically insulating enclosure disposed around the imaging element and including an insulating body in which the imaging element is disposed, the insulating body having a first recess formed therein; and
    a housing disposed around the electrically insulating enclosure,
    wherein a portion of the heat sink extends through the electrically insulating enclosure into contact with the housing, and
    wherein the portion of the heat sink directly engages the electrically insulating enclosure within the first recess formed in the insulating body.

2. The ultrasound imaging probe of claim 1, wherein the heat sink is formed of a ceramic material with a thermal conductivity of at least 2.0 watts/meter·Kelvin.

3. The ultrasound imaging probe of claim 2, wherein the ceramic material is selected from a group consisting of aluminum nitride, silicon nitride and silicon carbide.

4. The ultrasound imaging probe of claim 2, wherein the imaging element further comprises a heat conductive acoustic backing layer between the transducer element and the heat sink.

5. The ultrasound imaging probe of claim 1, wherein the electrically insulating enclosure comprises
a cover secured to the insulating body over the imaging element, the cover including a second recess aligned with the first recess to define an opening in the electrically insulating enclosure,
wherein the portion of the heat sink is positioned in engagement with the insulating body and the cover within the opening.

6. The ultrasound imaging probe of claim 1, wherein the housing is at least partially formed of a material with a thermal conductivity of at least 2.0 W/(mK).

7. The ultrasound imaging probe of claim 6, wherein the housing is formed of a metal.

8. The ultrasound imaging probe of claim 1, wherein the ultrasound imaging probe is an interventional ultrasound imaging probe.

9. The ultrasound imaging probe of claim 8, wherein the interventional ultrasound imaging probe is a transesophageal echocardiography probe.

10. The ultrasound imaging probe of claim 1, wherein the ultrasound imaging probe is a non-interventional ultrasound imaging probe.

11. The ultrasound imaging probe of claim 10, wherein the non-interventional ultrasound imaging probe is a transthoracic echocardiography probe.

12. An ultrasound imaging probe comprising:
an imaging element;
an electrically insulating enclosure disposed around the imaging element, the electrically insulating enclosure including an insulating body in which the imaging element is disposed, the insulating body having a recess formed therein, and a heat sink operably engaged with the imaging element, the heat sink formed of an electric insulating and heat conductive material; and
a heat conductive housing disposed around the electrically insulating enclosure and in contact with the heat sink,
wherein a portion of the heat sink extends through the electrically insulating enclosure into contact with the housing, and
wherein the portion of the heat sink directly engages the electrically insulating enclosure within the recess in the insulating body.

13. The ultrasound imaging probe of claim 12, wherein the heat conductive housing is formed of a metal.

14. The ultrasound imaging probe of claim 12, wherein the heat sink is formed of a ceramic material with a thermal conductivity of at least 2.0 W/(mK).

15. The ultrasound imaging probe of claim 12, wherein the ceramic material is selected from the group consisting of aluminum nitride, silicon nitride and silicon carbide.

16. An ultrasound imaging system comprising:
a processing unit configured to receive and process acquired ultrasound image data to create ultrasound images derived from the ultrasound image data;
a display operably connected to the processing unit to present the created ultrasound images to a user; and
an ultrasound imaging probe operably connected to the processing unit to obtain the ultrasound image data, the ultrasound imaging probe comprising:
an imaging element including:
a transducer element; and
a heat sink operably engaged with the transducer element, the heat sink formed of an electrically insulating and heat conductive material;
an electrically insulating enclosure disposed around the imaging element and including an insulating body in which the imaging element is disposed, the insulating body having an opening formed therein; and
a heat conductive housing disposed around the electrically insulating enclosure, wherein a side of the heat sink is engaged by and extends through the opening in the insulating body of the electrically insulating enclosure into contact with the housing.

17. The ultrasound imaging system of claim 16, wherein the heat sink is formed of a ceramic material.

18. The ultrasound imaging probe of claim 16, wherein the side of the heat sink directly engages the insulating enclosure.

* * * * *